United States Patent
Singh et al.

(10) Patent No.: US 10,006,014 B2
(45) Date of Patent: Jun. 26, 2018

(54) INSECTICIDAL CHITINASE PROTEIN ITS ENCODING NUCLEOTIDE AND APPLICATION THEREOF

(71) Applicant: Council of Scientific & Industrial Research, New Delhi (IN)

(72) Inventors: Pradhyumna K. Singh, Lucknow (IN); Santosh K. Upadhyay, Lucknow (IN); Chandrashekar Krishnappa, Lucknow (IN); Sharad Saurabh, Lucknow (IN); Rahul Singh, Lucknow (IN); Preeti Rai, Lucknow (IN); Harpal Singh, Lucknow (IN); Manisha Mishra, Lucknow (IN); Ajit P. Singh, Lucknow (IN); Praveen C. Verma, Lucknow (IN); Kuttan P. Narayanan, Lucknow (IN); Rakesh Tuli, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days. days.

(21) Appl. No.: 15/084,453

(22) Filed: Mar. 29, 2016

(65) Prior Publication Data
US 2016/0201044 A1   Jul. 14, 2016

Related U.S. Application Data

(62) Division of application No. 14/369,610, filed as application No. PCT/IN2012/000860 on Dec. 28, 2012, now abandoned.

(30) Foreign Application Priority Data
Dec. 28, 2011 (IN) ............... 3851/DEL/2011

(51) Int. Cl.
| | | |
|---|---|---|
| *C12N 15/00* | (2006.01) | |
| *C12N 15/63* | (2006.01) | |
| *C12N 9/10* | (2006.01) | |
| *C07H 21/04* | (2006.01) | |
| *C12N 9/42* | (2006.01) | |
| *A01N 63/00* | (2006.01) | |
| *C12N 15/82* | (2006.01) | |
| *A01N 37/46* | (2006.01) | |

(52) U.S. Cl.
CPC ........... *C12N 9/2442* (2013.01); *A01N 37/46* (2013.01); *A01N 63/00* (2013.01); *C12N 15/8286* (2013.01); *C12Y 302/01014* (2013.01); *C07K 2319/095* (2013.01)

(58) Field of Classification Search
CPC .. C12N 15/8286; C12N 9/2442; C12N 15/63; C12Y 302/01014; A01N 63/00
USPC ........ 435/320.1, 254.11, 209, 348; 536/23.1, 536/23.2; 800/302
See application file for complete search history.

(56) References Cited

U.S. PATENT DOCUMENTS

2015/0139976 A1*  5/2015  Singh ....................... 435/209

* cited by examiner

*Primary Examiner* — Robert B Mondesi
*Assistant Examiner* — Mohammad Y Meah
(74) *Attorney, Agent, or Firm* — Locke Lord LLP; Gabriel J. McCool

(57) ABSTRACT

A novel insecticidal chitinase protein from fern *Tectaria* sp., a process for preparation of the insecticidal protein and nucleic acid sequence encoding for said insecticidal protein and its application for insect control purposes.

10 Claims, 5 Drawing Sheets

INSECTICIDAL CHITINASE PROTEIN ITS ENCODING NUCLEOTIDE AND APPLICATION THEREOF

CROSS-REFERENCE

Figure 1:
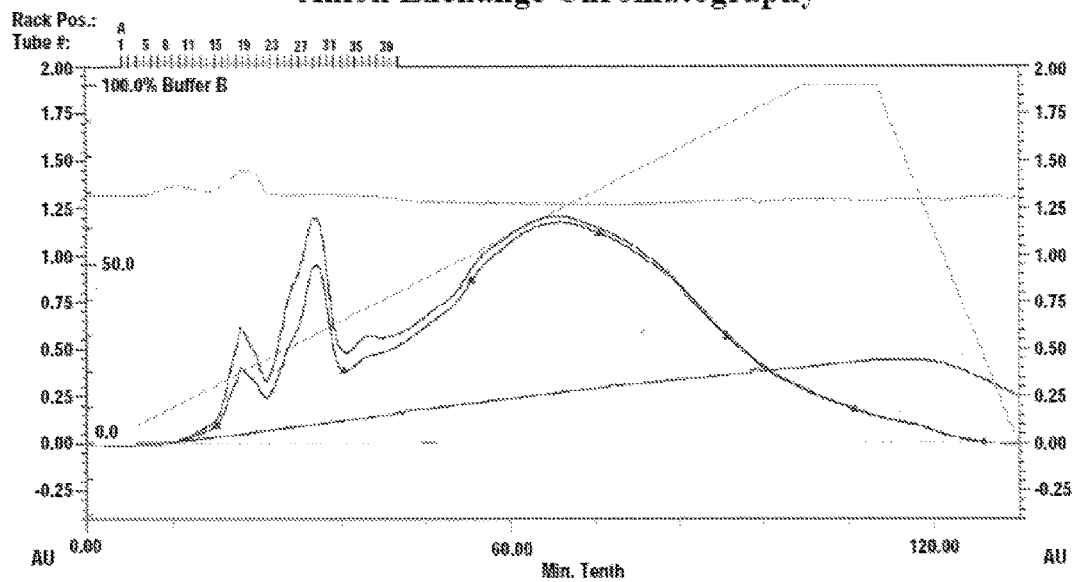
Figure 2:
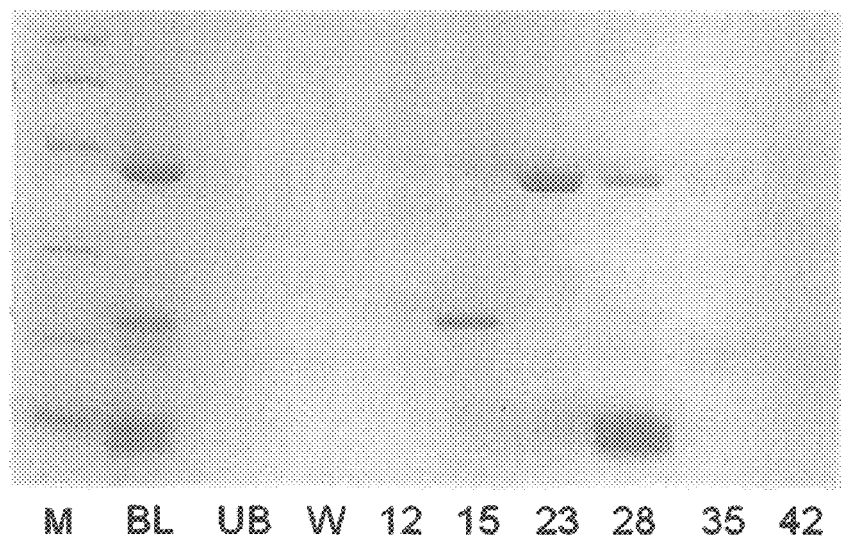

This application is the divisional of the national phase application Ser. No. 14/369,610 filed under 35 U.S.C. §371 of PCT International Application No. PCT/IN2012/000860, filed Dec. 28, 2012, which claims the benefit of Indian Patent Application No. 3851/DEL/2011, filed Dec. 28, 2011, the entire contents of the aforementioned applications are hereby incorporated herein by reference.

FIELD OF INVENTION

The invention relates to a novel insecticidal chitinase protein from fern *Tectaria* sp. process for preparation of the insecticidal protein and nucleic acid sequence encoding for said insecticidal protein and its application for insect control purposes.

BACKGROUND OF INVENTION

Loss of crop yields due to the attack of various insects is a worldwide problem. Insect pests are of mainly of two different types; biting and chewing type (e.g. Lepidopteran insects) & piercing and sucking type (Hemipteran insects). Transgenic insect resistant cultivars expressing *Bacillus thuringiensis* (Bt) protein have been developed for the control of insect pests of order Lepidoptera and Coleoptera group. However, the plants expressing Bt protein are not toxic to sap sucking pests. Hence, an alternative approach is required to control sap sucking pests. One of the approaches would be screening of plant biodiversity for insect toxic proteins.

DESCRIPTION OF THE RELATED ART

Ferns are the most ancient vascular plants. Fossil records of the ferns extend back to Devonian periods. Ferns are vascular plants, differing from the more primitive lycophytes in having true leaves, and they differ from seed plants (gymnosperms and angiosperms) in their mode of reproduction, absence of flowers and seeds. Ferns show great degree of diversity than any other plant phyla except angiosperms. Success of ferns is often attributed to their less susceptibility to insect attack. Although 9300 species of insects are reported to use ferns as a food source (Crooper-Driver 1978; Entomol. Exp. Appl. 24: 110-116), ferns have not been reported to suffer severe insect attacks, which is mainly due to the high concentration of secondary metabolites and possible presence of insect resistant macromolecules. Ferns are known to contain insect resistant secondary metabolites such as ferulic acid, hydrolysable tannins, terpenes, and alkaloids (Schaufelberger and Hostettmann, 1983; Planta Med. 48:105-107; Asakawa 1990; Biologically active substances from bryophytes. Pages 259-287. In: R chopra, B Satish (eds). Bryophyte development: Physiology and Biochemisrty. CRC, Boston.) and ecdysones mimics like insect hormone (Jones and Firn 1978; J Chem. Ecol. 4: 117-138; Lafont and Horn 1989. Phytoecdysteroids: structure and occurrence. Pages 39-64. In: J. Koolman (ed). Ecdysone: from chemistry to mode pf action. Thieme, Stuttgart.). Nevertheless ferns and mosses serve as the important source of insecticidal proteins, the crude protein extracts of several ferns and mosses caused 70-100% mortality of *Spodoptera frugiperda* and *Helicoverpa zea* and also resulted in significant growth reduction of both the insect species (Markham et al., 2006; Int. J. Plant Sci. 167: 111-117). Many insecticidal lectins have been isolated from ferns. Enzyme thiaminase derived form ferns and moss has been demonstrated for IR (Insect Resistance) activity. Thiaminase deterred feeding by southern armyworm *Nephrolepis exaltata* (Hendrix, 1977; Am. Nat. 115-171-196.).

Plants have evolved sophisticated defense mechanisms including a wide array of defensive compounds that confer resistance against phytophagous predators and infection by viruses, bacteria, fungi, nematodes, etc. The best known plant proteins supposedly involved in defense mechanisms are lectins, ribosome-inactivating proteins (RIPs) of types 1 and 2, inhibitors of proteolytic enzymes and glycohydrolases (Ryan, 1990; Annu. Rev. Phytopathol. 28, 425-449; Bowles, 1990; Ann. Rev. Biochem. 59, 873-907; Chrispeels and Raikhel, 1991; Plant Cell 3, 1-9; Barbieri et al., 1993; Biochem. J. 185, 203-210; Peumans and Van Damme, 1995; Plant Physiol. 109, 347-352.). Other plant proteins involved in the complex mechanisms of defense are the arcelins (Osborn et al., 1988; Science 240, 207-210.), chitinases (Herget et al., 1990; Mol. Gen. Genet. 224, 469-476), canatoxin (Carlini et al., 1997; J. Econ. Entomol. 90, 340-348.) and modified forms of storage proteins (Macedo et al., 1993; Comp. Biochem. Physiol. 105C, 89-94).

The chitin-binding plant proteins are defined as a group of protein comprising of chitinases, chitin-binding lectins and hevein (Raikel and Broekaert, 1991, in Control of plant gene expression, Verma DP (ed), Telford Press). All these proteins contain a conserved cysteine/glycine rich domain. This common region may confer the chitin binding activity. The domain is 40-43 amino acids in length and is either repeated twice, four-fold or fused to an unrelated domain. The chitin-binding plant proteins known to affect the growth of fungi or insects that contain chitin. However, the chitin binding proteins isolated from different sources differ in the specificity. The wheat/barley/rice-type lectins are toxic to insects, but are inactive to fungi in vitro (Murdock et al, 1990, Phytochem, 29: 85-89). The chitinases are inhibitory to the growth of certain pathogenic fungi. A chitinase with antifungal property has been isolated from the fern Pteris ryukyuensis (Onaga and Taira, 2008, Glycobiology, 18; 414-423).

Chitinases so far sequenced are classified into two different families, family 18 and 19, in the classification system of Glycoside hydrolases, based on amino acid sequence similarity of their catalytic module (Henrissat and Bairoch, 1993; Biochem. J. 293: 781-788: Davies and Henrissat, 1995, Structure, 3: 853-859). Family 18 contains chitinases from bacteria, fungi, viruses and some plant chitinases (class III and V) Family 19 contains plant chitinases (class I, II and IV), chitinases from purple bacteria, actinobacteria, certain nematodes, arthropods and protists (Udaya Prakash et al. 2010, J. Mol Evol. DOI 10.1007/s00239-010-9345-z). Plants synthesize various chitinases (Collinge et al. 1993, Plant J, 3: 31-40) and they are divided into five classes on the basis of their primary structures, independent of glycoside hydrolase classification (Kezuka et al. 2006, J. Mol. Biol, 358: 472-484).

Chitin-binding plant proteins are being used for the protection of plants against fungal disease and transgenic plants expressing chitin biding protein has been developed to confer resistance for fungal pathogen. U.S. Pat. No. 5,514,779 describes an antimicrobial protein which can be isolated from seeds of *Amaranthus*, seeds of *Capsicum* and seeds of *Briza*, has an amino acid sequence containing the common cysteine/glycine domain of Chitin-binding plant proteins and posses substantially better activity against plant pathogenic fungi than that of the Chitin-binding plant proteins. U.S. Pat. No. 6,710,228 discloses chimeric genes encoding lectins exhibiting insecticidal and/or fungicidal activity or which can be used to transform cotton to yield cotton cells, plants, and seeds in which the chimeric genes are expressed. The cotton embryogenic callus transformed, suppresses the growth of Heliothis larvae, and killed some larvae, when 25 mg of lyophilized transformed callus mixed into the artificial diet. U.S. Pat. No. 4,940,840 describe fungus (*Alternaria longipes*) resistant tobacco plants, expressing a chitinase gene from the bacterium *Serratia marcescens*. European Patent Application Number 418695 describes the use of regulatory DNA sequences from tobacco chitinase gene to drive expression of introduced genes producing transgenic plants with improved resistance to pathogens. Patent Application Number WO9007001 describes chitinase gene over-express transgenic plants for improved resistance to fungal pathogens.

The chitin binding proteins usually posses a catalytic module (CM) and one or two chitin binding module (CtBM). Class II chitinases of family 19 are known to lack CtBM and posses enzymatic activity (Udaya Prakash et al. 2010, J. Mol Evol. DOI 10.1007/s00239-010-9345-z), likewise chitinase (Chi NCTU2) from *Bacillus cereus*, belongs to family 18 also posses only CM (Yin-Cheng Hsieh et al., JBC. in Press. Aug. 4, 2010 as Manuscript M110.149310).

ADVANTAGES OVER THE PRIOR ART

The prior art lacks a chitinase with CtBM only (and lacking CM). No prior art is available on isolation of insecticidal Chitin-binding proteins from ferns. No experimental data is available to show the toxicity of any plant derived Chitin-binding proteins against sap sucking pest like whiteflies (*Bemisia tabaci*).

The Novelty of the Disclosed Protein Has Been Established on the Basis of Below Mentioned Points i. No prior art is available on isolation of insecticidal Chitin-binding proteins from ferns and no experimental data available so far to show the toxicity of any Chitin-binding proteins against sap sucking pest like whiteflies (*Bemisia tabaci*).

ii. Blast analysis of the insecticidal protein disclosed in present invention shows homology with the chitin binding domain of chitinase super family III and lacks a typical catalytic module. However, the primary structure of the chitinase in present invention does not show significant homology with any plant derived chitin binding protein or chitinase in the available database.

iii. The chitin binding proteins usually posses a catalytic module (CM) and one or two chitin binding module (CtBM). Class II chitinases of family 19 are known to lack CtBM, possesses catalytic module (CM) and show enzymatic activity (Udaya Prakash et al. 2010, J. Mol Evol. DOI 10.1007/s00239-010-9345-z). Likewise chitinase (Chi NCTU2) from *Bacillus cereus*, belonging to family 18 also possesses CM only (Yin-Cheng Hsieh et al., JBC. in Press. Aug. 4, 2010 as Manuscript M110.149310). The protein disclosed in the present invention contains only CtBM and still shows chitinase activity. This is the first report of chitinase which possesses only CtBM and lacks distinct CM. This makes the isolated chitinase novel.

OBJECT OF THE INVENTION

The object of the present invention is to provide insecticidal Chitinase proteins having a chitin binding module and lacking Catalytic Module, from fern *Tectaria* sp.

Another object of present invention is to prepare the said insecticidal chitinase protein.

Another object of the present invention is to isolate pure insecticidal chitinase protein from fern *Tectaria* sp. and to prepare nucleic acid sequence encoding the said insecticidal protein.

Still another object of the present invention is to prepare recombinant chitinase protein having CtBM only and lacking CM for its application for insect control purposes.

SUMMARY OF THE INVENTION

Accordingly, the present invention is directed to novel insecticidal Chitinase proteins from fern *Tectaria* sp., having a chitin binding module and lacking Catalytic Module a process for preparation of the insecticidal protein and to prepare nucleic acid sequence encoding the said insecticidal protein to produce recombinant chitinase proteins which substantially obviate one or more problems due to limitations of the related art. These and other features, aspects and advantages of the present invention will be better understood with reference to the following description, drawings and claims.

BRIEF DESCRIPTION OF FIGURES

FIG. 1: chromatogram of the protein fraction separated on Q-sepharose (fast flow) column. The arrow indicates the fractions showing high insecticidal activity.

FIG. 2: SDS-PAGE of protein fraction separated on Q-sepharose (fast flow) column M: marker, BL: before loading, UB and W: Unbound proteins, 12-42 different fractions eluted from column.

FIG. 3: Purified protein separated on 2-D PAGE.

FIG. 4: MALDI-TOF-TOF analysis of the isolated protein

FIG. 5: Expression and purification of the insecticidal protein of *Tectaria* in *E. coli*. M: protein molecular weight marker; lane 1, uninduced sample; lane 2, 1 h post induction; lane 3, 2 h post induction; lane 4, 3 h post induction; lane 5, Ni-NTA purified protein; lane 6, fusion protein digested with SUMO-Protease I; lane 7, Negative purification of insecticidal protein on Ni-NTA. Arrowhead in lanes 2-5 indicates the desired fusion protein and in lanes 6 and 7 indicates desired protein after digestion with SUMO protease and after purification, respectively.

FIG. 6: pepsin digestibility and thermal stability of the insecticidal protein.

DETAILED DESCRIPTION OF THE INVENTION

The present invention provides purification and isolation of insecticidal chitinase protein from the fern *Tectaria* sp. process for preparation of an insecticidal protein isolated from the fern *Tectaria* sp. and DNA sequence encoding the said protein. The insecticidal protein was purified from leaves of *Tectaria* sp. The method of protein purification involves, extraction of total soluble protein; fractionation of crude extract using differential ammonium sulfate precipitation and different steps of chromatography. Each stage of purification was guided by insecticidal activity. The protein defined as insecticidal protein is toxic to at least one of the insects-whitefly (*Bemisia tabaci*), cotton boll worm (*Helicoverpa armigera*), aphid (*Aphis gossypii*) and *Spodoptera litura*. Insecticidal activity includes a range of antagonistic effects such as mortality (death), growth reduction and feeding deterrence. Gene encoding the purified insecticidal protein was cloned using N-terminal sequencing data of the purified protein by designing degenerate primers. The pI of the protein was in range of 5-6. The protein is of 216 amino acids (Sequence I.D. No. 4) and the mature peptide is of 192 amino acids (Sequence I.D. No. 5) with respective molecular weight of 23.684 kDa and 21.270 kDa. The cloned cDNA consisted of 828 nucleotides (Sequence I.D. No. 1), of which the protein encoding ORF sequence was of 651 nucleotides (Sequence ID No. 2) and the mature peptide encoding ORF is of 579 nucleotides (Sequence ID No. 3). The gene encoding the insecticidal protein was cloned in *E. coli* and plant expression vector. The insecticidal protein was expressed in *E. coli* and purified. Like native protein, the recombinant protein also showed the insecticidal activity. The purified native protein as well as the recombinantly expressed protein showed the chitinase activity. The amino acid sequence of the protein was compared with the available data base of chitinases by BlustlW analysis, to establish its novelty. The bio-safety of the protein was evaluated using online allergic domain search and pepsin digestibility test. The protein has no allergic domains and hence does not cause any allergic response and is quickly digested by enzyme pepsin. This indicated bio-safety of the protein.

Accordingly present invention provides an isolated novel insecticidal protein characterized in that it contain chitin binding module without having catalytic module, from fern *Tectaria* sp., process for preparation of the insecticidal chitinase protein comprising the step of:
  (a) isolating chitinase protein from leaf of fern *Tectaria* sp. in a manner such as herein described,
  (b) cloning c-DNA from purified protein, using N-terminal sequencing data of the purified protein by designing degenerate primers,
  (c) identifying ORF sequence encoding mature polypeptide of insecticidal chitinase from cloned cDNA sequence,
  (d) cloning the DNA encoding the insecticidal protein in *E. coli* expression vector in fusion with SUMO peptide to get expression of recombinant protein followed by purification of recombinant protein by conventional manner.

In the embodiment of the invention, the nucleotide sequence encoding an insecticidal protein as shown in sequence SEQ ID No. 1 or SEQ ID No. 2 or SEQ ID No. 3.

In the other embodiment of the invention, the amino acid residues of the insecticidal polypeptide is shown in sequences SEQ ID No. 4 or SEQ ID No. 5.

In yet another embodiment of the invention, the insecticidal protein can be produced by the expression of recombinant DNA.

In the further embodiment of the invention, the plant expression cassette containing the nucleotide encoding the insecticidal protein is useful for transformation of cotton and other crop plants for the development of transgenic plants resistant to whiteflies.

Ferns are vascular plants differing from the more primitive lycophytes in having true leaves, and seed plants (gymnosperms and angiosperms) in their mode of reproduction, absence of flowers and seeds. Ferns show great degree of diversity than any other plant phyla except angiosperms. Success of ferns is often attributed to their less susceptibility to insect attack. These have not been reported to suffer from severe insect attacks, which is mainly due to the high concentration of secondary metabolites and possible presence of insect resistance macromolecules. Ferns are known to contain insect resistant secondary metabolites such as ferulic acid, hydrolysable tannins, terpenes, alkaloids and ecdysones that mimic insect hormones. The crude protein extracts of several ferns and mosses caused mortality and also significant growth reduction of insects. Many insecticidal lectin proteins have been isolated from ferns.

Figure 3:
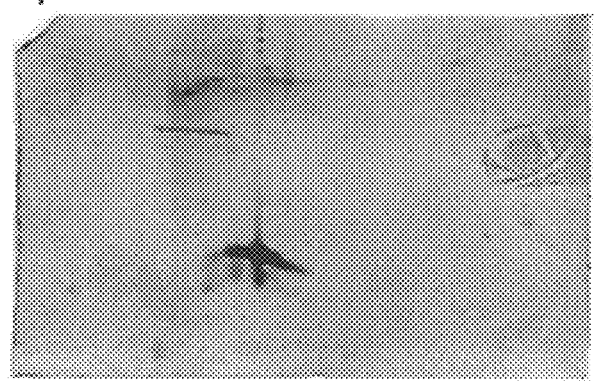
Figure 4:
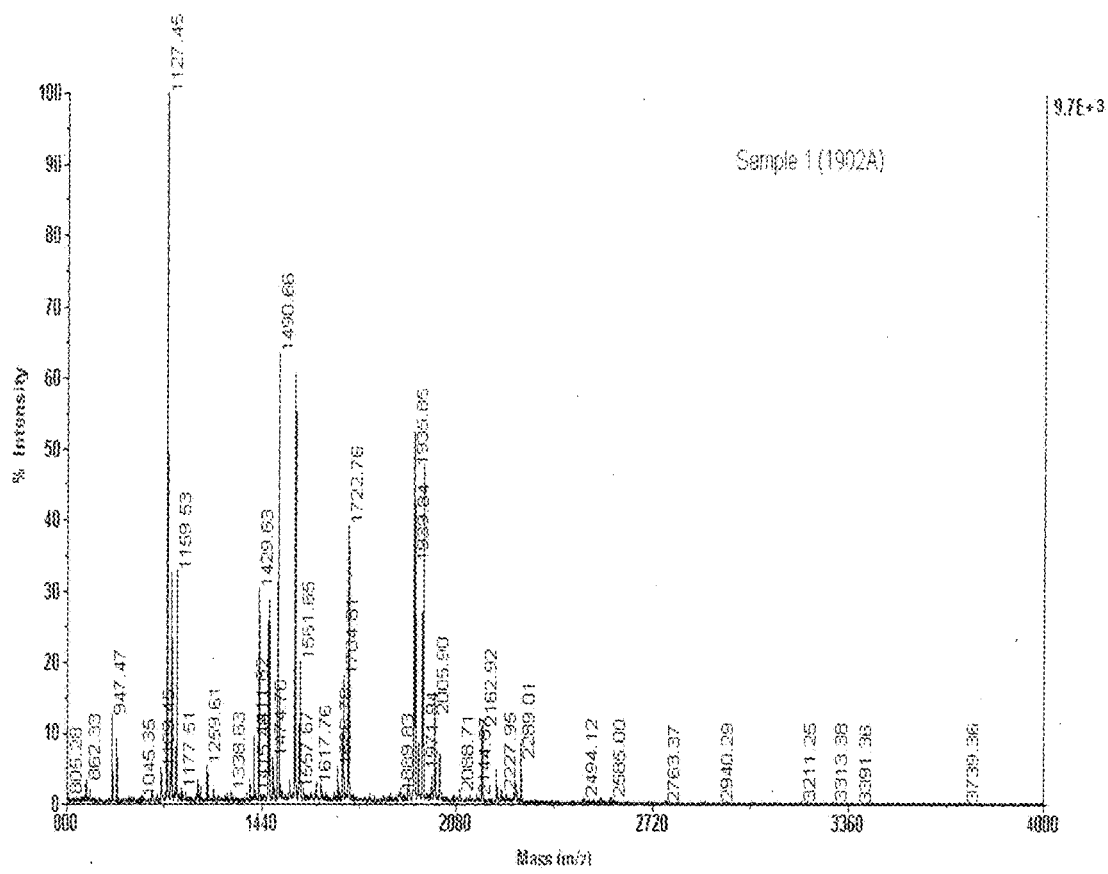
Figure 5:
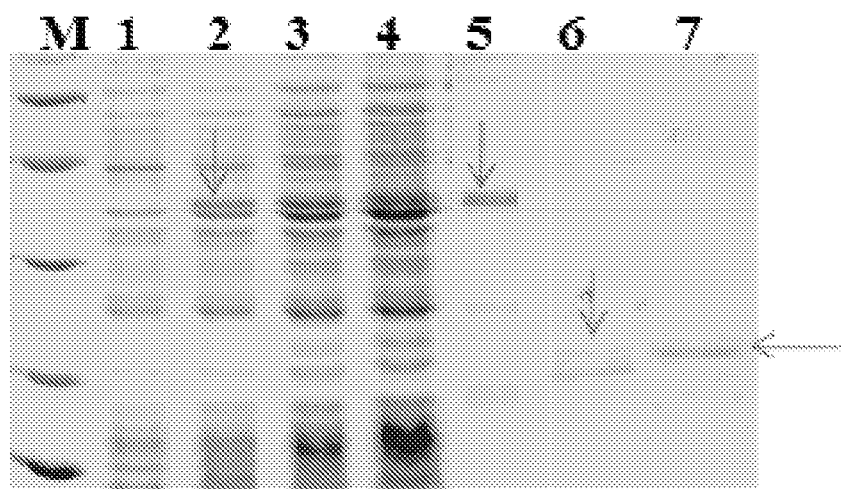

In this present invention, we purified a new insecticidal protein from the leaves of fern *Tectaria*. The method of insecticidal activity guided purification of protein involved extraction of total soluble protein from leaves; fractionation of total soluble protein with differential ammonium sulfate precipitation and further purification involving different chromatography as explained in detail (Example 1). At each stage of purification, every fraction was dialyzed, evaluated for insecticidal activity and the fractions which were found effective were taken to the next step of purification. The purified protein was evaluated for toxicity against whiteflies (*Bemisia tabaci*) by incorporating the protein in the artificial diet (Example 4). The protein caused mortality of whiteflies (Table 2). The purity and pI of the purified insecticidal protein was further determined by 2-D PAGE (FIG. 3). The purified protein was subjected to Mass Spectrometric analysis and N-terminal sequencing (Example 2). Mass spectrometric analysis on MALDI-TOF TOF platform (FIG. 4) established novelty of the molecule. Its insecticidal activity has not been reported earlier. The degenerate primers were designed using the N-terminal sequencing data (Table 1) and the gene encoding protein was cloned from the cDNA, synthesized from the total RNA, isolated from the plant leaves (Example 3). The protein was of 216 amino acid residues (Sequence ID No. 4) and the mature peptide of 192 amino acid residues (Sequence ID No. 5) with respective molecular weight of 23.684 kDa and 21.27 kDa. The cloned cDNA consisted of 828 nucleotides (Sequence ID No. 1), of which protein encoding ORF sequence is of 651 nucleotides (Sequence ID No. 2) and mature peptide encoding ORF is of 579 nucleotides (Sequence ID No. 3).

The gene encoding the insecticidal protein was cloned in *E. coli* expression vector in fusion with SUMO peptide and the recombinant protein was expressed and purified (Example 5). The recombinant protein also showed the insecticidal activity against whiteflies.

In the embodiment of the invention, the nucleotide sequence encoding an insecticidal protein as shown in sequence SEQ ID No. 1 or SEQ ID No. 2 or SEQ ID No. 3. In the other embodiment of the invention, the amino acid residues of the insecticidal protein is shown in sequences SEQ ID No. 4 or SEQ ID No. 5.

In another embodiment of the invention, an isolated protein as claimed in claim 1 is toxic to whitefly (*Bemisia tabaci*).

In yet another embodiment of the invention, the protein can be used for the control of other insect pests.

The preferred use of the protein according to the invention is to insert the genes encoding these proteins into the plants using various methods available for the introduction and expression of the foreign genes in transgenic plants. The method of gene insertion and expression may include methods such as *Agrobacterium* mediated gene transfer, microinjection of DNA into cells or protoplasts, DNA transfer via growing pollen tubes, DNA uptake by imbibing zygotic embryos, silicon carbide fiber mediated delivery, microprojectile bombardment and direct DNA uptake employing polyethylene glycol, liposomes or electroporation. Once a line of transgenic plants is established, the character may be transferred to other cultivars by conventional plant breeding.

Plants which can be protected, preferably by transformation, according to the methods of this invention include, but are not limited to rice, wheat, maize, cotton, potato, sugarcane, tobacco, soybean, cabbage, cauliflower, beans, apple, tomato, mustard, rape seed and sunflower etc.

The protein useful in insect control and the corresponding genes can be obtained from, all the above ground and below ground plant parts of any fern not necessarily limited to *Tectaria* sp.

In yet another embodiment of the invention, an insecticidal protein can be produced by the expression of recombinant DNA.

In further embodiment of the invention, the gene encoding the insecticidal protein was cloned in *E. coli* expression vector in fusion with SUMO peptide. The recombinant insecticidal protein was expressed in *E. coli* and purified by affinity chromatography.

The recombinant protein was digested with SUMO-Protease I to liberate the desired protein from SUMO peptide. The recombinant protein also showed the insecticidal activity against whiteflies.

In the further embodiment of the invention, the plant expression cassette was transformed in cotton for the development of transgenic plants resistant to whiteflies.

In still another embodiment of the invention, the protein is biologically safe to use because it can be completely digested by pepsin in less than 30 seconds under the experimental conditions i.e.; at pH 1.2 and pH 2.0 SGF buffer. The online search using allergen data revealed that the protein has no allergic domains and does not cause any allergic responses.

Example 1

Extraction of Total Soluble Protein and Insecticidal Activity Guided Purification Plant material was collected from the fern house of National Botanical Research Institute, Lucknow, India. Total soluble protein was prepared by following the procedures of Markham et al., (2006). Leaves were crushed into fine powder under liquid nitrogen. Powdered leaf was suspended in ice cold protein extraction buffer (20 mM HEPES, 0.5 mM DTT, 1 mM EDTA, 10% glycerol, 1 mM phenylmethylsulfonylfluoride and 1 mm benzamidine, pH 8.0) in 1:4 (w/v) ratio. The suspension was homogenized at 4° C. and incubated for 1 h and then filtered through cheesecloth. The homogenate was centrifuged (3000×g, 4° C., 30 min) The total soluble protein was fractionated with differential ammonium sulfate precipitation at the interval of 20% saturation. Each fraction was dialyzed and evaluated for insecticidal activity. The effective fraction was further dialyzed in 20 mM TrisCl (pH 8.0) and loaded on Q sepharose (FF) column, pre-equilibrated with 20 mM TrisCl (pH 8.0). The column was washed with the same buffer until $OD_{280}$ reached to less than 0.02. The column bound proteins were eluted with a linear gradient of 0-1 M NaCl in 20 mM TrisCl (pH 8.0). The eluted fractions were dialyzed against 20 mM TrisCl (pH 8.0) and used for insect bioassay. Fractions causing mortality to the insect were pooled and dialyzed against 20 mM Tris (pH 8.0) containing 200 mM NaCl. The pooled protein sample was resolved on Superdex 200 equilibrated with protein sample buffer. Eluted fractions were again dialyzed to remove salt and insect bioassay was performed. Purified insecticidal protein was further analysed by 2 dimensional gel electrophoresis for purity and pI determination. The pI of the protein was between 5-6.

Example 2

Peptide Mass Finger Printing and N-Terminal Sequencing

Peptide Mass Finger Printing:

The purified protein was electrophorased on SDS-PAGE. The protein band was cut and digested with trypsin and used for peptide mass finger printing. The data was analyzed on MASCOT search. No match with the peptide/protein was found in the database.

N-Terminal Sequencing:

For N-terminal sequencing, the purified protein was run on SDS-PAGE and transferred onto the PVDF membrane and used for N-terminal sequencing.

TABLE 1

| N-terminal sequencing data of the insecticidal protein<br>Position 1st choice 2nd choice, X - no clear signal |
|---|
| 1. H |
| 2. G |
| 3. S |
| 4. M |
| 5. E |
| 6. D |
| 7. P |
| 8. I |
| 9 S |
| 10. X R |
| 11. X V |
| 12. X Y |
| 13. X Y |
| 14. X Y, R |
| 15. X |
| 16. X |
| 17. X L |
| 18. X E |

Example 3

Cloning of the Toxin Encoding Gene

Total RNA was isolated from the plant leaves. The cDNA synthesis was performed for 5' and 3' rapid amplification of cDNA ends. For 3' RACE, RNA was reversely transcribed with the 3' RACE CDS Primer A. The primary PCR was performed with degenerate primer (designed on the basis of N-terminal sequencing data) and Universal primer A mix. For 5' RACE, RNA was reversely transcribed with the 5' RACE CDS Primer and SMART II A Oligonucleotide. Based on the sequence of the 3' RACE product, the gene specific primers (GSP1 and GSP2) were designed and synthesized. The first round of PCR was performed with GSP1 and Universal Primer A Mix (UMP, provided in the kit). The PCR product was diluted 50-fold for a second round of amplification of the gene with GSP2 and Nested Universal Primer A (NUP).

Example 4

Insect Bioassay Against Whiteflies (*Bemisia tabaci*)

Bioassay was carried out with >1 day old adult whiteflies (*Bemisia tabaci*). Whiteflies were reared on cotton plants grown in pots in the laboratory at 26±2° C. and 80% relative humidity. Cotton plants having large number of nymphs and pupae were selected, adult whiteflies were removed and plants were kept in isolation for the emergence of fresh adults. Bioassays were carried out as per Upadhyay et al., 2011 (J. Biosciences. 36: 153-161). The whiteflies were directly collected into specimen tubes. The leaf containing freshly emerged adults was kept close to the open end of the tube. Insects were stimulated to move inside the tube by gentle tapping (FIG. 1). After the collection of whiteflies, tubes were capped and kept in inverted position. Artificial diet (with/without insecticidal protein) was filter sterilized through syringe filter (0.22 μm) and sandwiched (100 μl) between the two layers of sterilized stretched parafilm on inner surface of the sterile specimen tube caps aseptically. The caps of the bioassay tubes containing insects were replaced with the diet containing caps. The tubes were kept in upright position so that the caps faced toward light. The old caps were replaced with caps containing fresh diet of respective test sample on alternate days to minimize the chances caused by degradation of test sample and contamination in diet. Perforations were made on the bioassay vial for air exchange.

TABLE 2

Toxicity of purified protein against whitefly (*Bemisia tabaci*)

| Protein conc. | % Mortality | | | | | |
|---|---|---|---|---|---|---|
| μg/ml | $2^{nd}$ day | $3^{rd}$ day | $4^{th}$ day | $5^{th}$ day | $6^{th}$ day | $7^{th}$ day |
| 100 | 87.5 | 96.87 | 100 | — | — | — |
| 50 | 56.75 | 78.37 | 93.7 | 100 | — | — |
| 25 | 16.07 | 56.75 | 78.37 | 94.64 | 100 | — |
| 12 | 15.62 | 21.87 | 28.12 | 53.12 | 62.5 | 76.34 |
| 5 | 13.15 | 15.78 | 21.05 | 28.94 | 31.57 | 36.84 |
| 2 | 13.63 | 13.63 | 22.72 | 27.27 | 27.27 | 34.09 |
| Control | 0 | 6.25 | 9.37 | 12.5 | 18.75 | 18.75 |

Example 5

Expression and Purification of Insecticidal Protein in *E. coli*

The gene encoding the insecticidal protein was cloned in *E. coli* expression vector in fusion with SUMO peptide under T7 promoter. The recombinant insecticidal protein was expressed after induction with IPTG and expression profile was observed for every hour after induction for 3 h. After 3 h of induction, the cells were harvested by centrifugation and lysed by lysozyme and broken by sonication. The inclusion bodies containing the desired protein were washed with 20 mM TrisCl (pH 8).

The inclusion bodies were again suspended in 20 mM Tris (pH 8) containing 8M Urea and kept at room temperature for 2 h for solubilization. The suspension was centrifuged (13000×g, 15 min, room temperature) and supernatant was collected. The recombinant protein was purified by Ni-affinity chromatography in denatured condition. The purified recombinant protein was refolded. The protein was dialyzed in PBS and digested with SUMO-Protease I to liberate the desired protein from SUMO peptide. The purified insecticidal recombinant protein was tested in insect bioassay.

Example 6

Biosafety Evaluation of the Insect Toxic Protein

Figure 6:
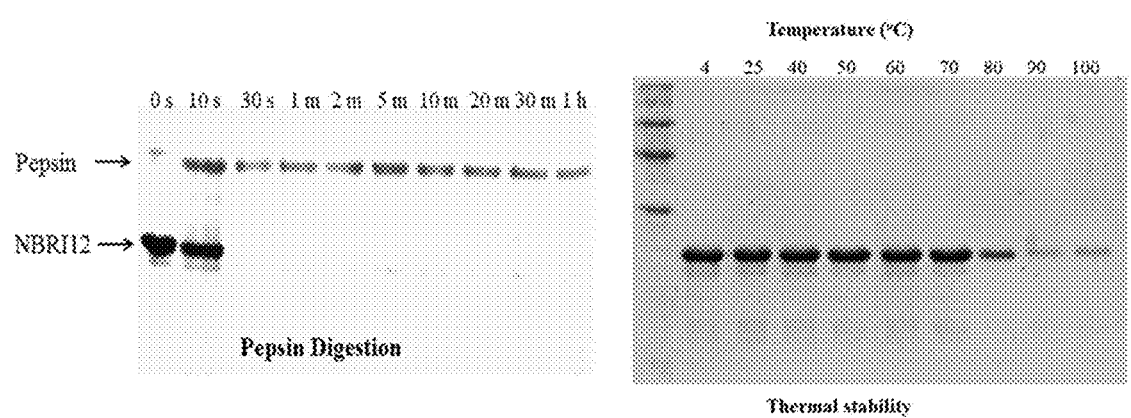

The biosafety of protein was evaluated using online allergic domain search and pepsin digestibility test.
Allergen Search
The online search using allergen data based revealed that the protein has no allergic domains and therefore expected not to cause allergic responses.
Pepsin Digestibility
Purified porcine pepsin has been used to evaluate the stability of a number of food allergens and non-allergenic proteins in a multi-laboratory study that demonstrated the rigor and reproducibility in nine laboratories (Thomas et al 2004., Regulatory Toxicology and Pharmacology, 37:87-98). Porcine pepsin is an aspartic endopeptidase with broad substrate specificity. Pepsin is optimally active between pH 1.2 and 2.0, but inactive at pH 3.5 and irreversibly denatured at pH 7.0. The assay is performed under standard conditions of 10 units of pepsin activity per microgram of test protein. The original assay described by Astwood et al. (Nature Biotechnology, 14:1269-1273, 1996) recommends performing the digestion at pH 1.2. However, the FAO/WHO (2001) recommends using two pH conditions (pH 1.2 and pH 2.0). The assay is performed at 37° C. and samples are removed at specific times (0, 0.5, 1, 2, 5, 10, 20, 30, 60 minutes) and the activity of pepsin is quenched by neutralization with carbonate buffer and sodium dodecyl sulfate (SDS-) polyacrylamide gel electrophoresis (PAGE) loading buffer and heating at >70° C. for 3-5 minutes. The timed digestion samples are electrophorased on SDS-PAGE and stained with Coomassie Brilliant Blue to evaluate the extent of digestion. Assessment of the digestibility assays developed by Bannon et al. (2002, Comments Toxicol. 8:271-285.) and by Thomas et al. (2004) indicate that the most of the non-allergenic food proteins are digested in approximately 30 seconds, while the major food allergens are stable, or produce pepsin-stable fragments that are detectable for 8-60 minutes. The protein was completely digested by pepsin in less than 30 seconds under both the experimental conditions (at pH 1.2 and pH 2.0 SGF buffer).
Thermal Stability
A 1 mg/ml solution of the protein was prepared in 20 mM TrisCl (pH 8.0). The protein was incubated at the 30° C., 40° C., 50° C., 60° C., 70° C., 80° C., 90° C. and 100° C. 2.5 μl aliquot that contained 2.5 μg of protein was analyzed on a 12% SDS-PAGE gel. The experiment was performed in triplicate. 2.5 μg of treated protein was used for the enzymes assay also. The protein was found unstable at the temperatures beyond 90° C. (FIG. 6)

```
Nucleotide sequence of the complete cDNA of the bio-active
protein encoding gene
                                                Sequence I.D.NO. 1
          acgcggggat cggtcatagt gtgagccttg aggatgggga ggtcatgggg agttgtggct    60
gttatggtgt tgtgcgccag tggcctgctg ggcatagtgc gcggccatgg cagcatggaa   120 gacccatca gtcgcgtcta cagatgccgt ctagagaatc cggagcgtcc cacgtcgcca   180
```

-continued

```
gcttgccaag cggcggtggc gctcagtggc actcaagcct tctatgattg gaatgaggcg  240
aacattccta acgccgctgg ccggcaccgc gagctcattc cggatggcca actgtgcagc  300
gccgggcggt tcaagtttcg gggcctcgac ttggcacgct ccgactggat agccacccc   360 tcgccctccg gcgccagcag cttcccattc cgctacatag ccaccgccgc gcacttgggc  420
ttcttcgagt tctacgtcac cagggaaggt taccagccca ctgtaccgct taaatgggca  480
gacttggagg agttgccgtt catcaacgtc accaaccccc cgcttgtcag cggctcctac  540
caaatcaccg gcaccacgcc ttcctgcaag tccggcagcc acgtcatgta cgtcatatgg  600
cagcgcaccg acagcccga agccttccac tcctgctccg acgtctactt cactgatgcc  660
ctctctctcc actctaccac ctaggaggag gcgctctgt tgggccactt ctctctctct  720
ctctctctct ctctctcggg gcagtgctct cgtgctcgga atgctcctgt aattacaata  780
agaaatgaac atgtttcttt cgcctctcta aaaaaaaaaa aaaaaaa.            828
```

20

Protein coding ORF sequences was were predicted by ORF finder software of NCBI

Nucleotide sequence of the full-length bioactive protein encoding ORF

Sequence ID No. 2
```
atggggaggt catggggagt tgtggctgtt atggtgttgt gcgccagtgg cctgctgggc   60
atagtgcgcg gccatggcag catggaggac cccatcagtc gcgtctacag atgccgtcta  120
gagaatccgg agcgtcccac gtcgccagct tgccaagcgg cggtggcgct cagtggcact  180
caagccttct atgattggaa tgaggcgaac attcctaacg ccgctggccg gcaccgcgag  240
ctcattccgg atggccaact gtgcagcgcc gggcggttca agtttcgggg cctcgacttg  300
gcacgctccg actggatagc cacccctcg ccctccggcg ccagcagctt cccattccgc  360
tacatagcca ccgccgcgca cttgggcttc ttcgagttct acgtcaccag gaaggttac   420 cagcccactg taccgcttaa atgggcagac ttggaggagt tgccgttcat caacgtcacc  480
aaccccccgc ttgtcagcgg ctcctaccaa atcaccggca ccacgccttc ctgcaagtcc  540
ggcagccacg tcatgtacgt catatggcag cgcaccgaca gccccgaagc cttccactcc  600
tgctccgacg tctacttcac tgatgccctc tctctccact ctaccaccta g.          651
```

Nucleotide sequence encoding mature bio-active protein

Sequence ID No. 3
```
catggcagca tggaggaccc catcagtcgc gtctacagat gccgtctaga gaatccggag   60
cgtcccacgt cgccagcttg ccaagcggcg gtggcgctca gtggcactca agccttctat  120
gattggaatg aggcgaacat tcctaacgcc gctggccggc accgcgagct cattccggat  180
ggccaactgt gcagcgccgg gcggttcaag tttcggggcc tcgacttggc acgctccgac  240
tggatagcca ccccctcgcc ctccggcgcc agcagcttcc cattccgcta catagccacc  300
gccgcgcact tgggcttctt cgagttctac gtcaccaggg aaggttacca gcccactgta  360
ccgcttaaat gggcagactt ggaggagttg ccgttcatca acgtcaccaa ccccccgctt  420
gtcagcggct cctaccaaat caccggcacc acgccttcct gcaagtccgg cagccacgtc  480
atgtacgtca tatggcagcg caccgacagc cccgaagcct tccactcctg ctccgacgtc  540
tacttcactg atgccctctc tctccactct accacctag.                         579
```

ORF sequence was translated to the amino acid sequences by Expasy translate tools http://www.expasy.ch/tools/dna.html.

```
Amino acid sequence of the full-length bio-active protein
                                                     Sequence ID No. 4
MGRSWGVVAV MVLCASGLLG IVRGHGSMED PISRVYRCRL ENPERPTSPA CQAAVALSGT    60

QAFYDWNEAN IPNAAGRHRE LIPDGQLCSA GRFKFRGLDL ARSDWIATPS PSGASSFPFR   120

YIATAAHLGF FEFYVTREGY QPTVPLKWAD LEELPFINVT NPPLVSGSYQ ITGTTPSCKS   180

GSHVMYVIWQ RTDSPEAFHS CSDVYFTDAL SLHSTT.                            216
```

Amino acid sequences was further analyzed by signal iP software http://www.cbs.dtu.dk/services/SignalP/ for signal peptide. Signal peptide was 24 amino acid long.

```
Amino acid sequence of the mature bio-active protein
                                                     Sequence ID No. 5
HGSMEDPISR VYRCRLENPE RPTSPACQAA VALSGTQAFY DWNEANIPNA AGRHRELIPD    60

GQLCSAGRFK FRGLDLARSD WIATPSPSGA SSFPFRYIAT AAHLGFFEFY VTREGYQPTV   120

PLKWADLEEL PFINVTNPPL VSGSYQITGT TPSCKSGSHV MYVIWQRTDS PEAFHSCSDV   180

YFTDALSLHS TT.                                                      192
```

The invention claimed is:

1. A cDNA molecule encoding an insecticidal chitinase protein containing chitin binding module but lacking catalytic module wherein the nucleotide sequence encoding the insecticidal protein is comprised by any one of the SEQ ID NO. 1 or SEQ ID NO. 2 or SEQ ID NO. 3 and amino acid sequence of the insecticidal protein is comprised by any one of the sequences SEQ ID NO. 4 or SEQ ID NO. 5.

2. The cDNA molecule of claim 1, wherein said insecticidal chitinase protein is of 216 amino acid residues long pro-protein and 192 amino acid residues long mature protein with respective molecular weight 23.684 and 21.270 kDa.

3. The cDNA molecule of claim 1, wherein said insecticidal chitinase protein comprises of chitin binding module (CtBM), and shows exo- and endo-chitinase activity.

4. The cDNA molecule of claim 1, wherein the said insecticidal chitinase protein consists of chitin binding module (CtBM), and shows exo- and endo-chitinase activity.

5. The cDNA molecule of claim 1, wherein the said insecticidal chitinase protein is useful for the control of insects from order homoptera, heteroptera, diptera, coleoptera and lepidoptera, particularly toxic to white fly (*Bemisia tabaci*).

6. A process for preparation of the insecticidal chitinase protein encoded by the cDNA molecule of claim 1, comprising the steps of:

(i) isolating chitinase protein from fern *Tectaria* sp. in a manner such as herein described, (ii) cloning the cDNA of claim 1 from purified protein, using N-terminal sequencing data of the purified protein by designing degenerate primers, (iii) identifying ORF sequence encoding a mature polypeptide of insecticidal chitinase from cloned cDNA sequence, (iv) cloning the cDNA encoding the insecticidal protein in an *E. coli* expression vector in fusion with SUMO peptide to get expression of recombinant protein followed by purification of recombinant protein by conventional manner.

7. The process as claimed in claim 6, wherein the insecticidal protein is being produced by expressing its encoding nucleotide in homologous or heterologous system using recombinant DNA technology.

8. A transgenic crop comprising the cDNA molecule encoding an insecticidal chitinase protein according to claim 1, wherein the transgenic crop expresses the insecticidal chitinase protein causing toxicity to insect and exhibiting protection against insect pest.

9. An expression vector comprising the cDNA molecule encoding an insecticidal chitinase protein according to claim 1.

10. A method of controlling insects using the cDNA molecule encoding an insecticidal chitinase protein according to claim 1.

* * * * *

SEQUENCE LISTING

```
<160> NUMBER OF SEQ ID NOS: 5

<210> SEQ ID NO 1
<211> LENGTH: 828
<212> TYPE: DNA
<213> ORGANISM: Tectaria sp.
<220> FEATURE:
<221> NAME/KEY: CDS
<222> LOCATION: (34)..(681)

<400> SEQUENCE: 1
acgcggggat cggtcatagt gtgagccttg agg atg ggg agg tca tgg gga gtt      54
                                    Met Gly Arg Ser Trp Gly Val
                                      1               5 gtg gct gtt atg gtg ttg tgc gcc agt ggc ctg ctg gca ata gtg cgc     102
Val Ala Val Met Val Leu Cys Ala Ser Gly Leu Leu Gly Ile Val Arg
         10                  15                  20 ggc cat ggc agc atg gag gac ccc atc agt cgc gtc tac aga tgc cgt     150
Gly His Gly Ser Met Glu Asp Pro Ile Ser Arg Val Tyr Arg Cys Arg
 25                  30                  35 cta gag aat ccg gag cgt ccc acg tcg cca gct tgc caa gcg gcg gtg     198
Leu Glu Asn Pro Glu Arg Pro Thr Ser Pro Ala Cys Gln Ala Ala Val
 40                  45                  50                  55 gcg ctc agt ggc act caa gcc ttc tat gat tgg aat gag gcg aac att     246
Ala Leu Ser Gly Thr Gln Ala Phe Tyr Asp Trp Asn Glu Ala Asn Ile
                 60                  65                  70 cct aac gcc gct ggc cgg cac cgc gag ctc att ccg gat ggc caa ctg     294
Pro Asn Ala Ala Gly Arg His Arg Glu Leu Ile Pro Asp Gly Gln Leu
             75                  80                  85 tgc agc gcc ggg cgg ttc aag ttt cgg ggc ctc gac ttg gca cgc tcc     342
Cys Ser Ala Gly Arg Phe Lys Phe Arg Gly Leu Asp Leu Ala Arg Ser
         90                  95                 100 gac tgg ata gcc acc ccc tcg ccc tcc ggc gcc agc agc ttc cca ttc     390
Asp Trp Ile Ala Thr Pro Ser Pro Ser Gly Ala Ser Ser Phe Pro Phe
    105                 110                 115 cgc tac ata gcc acc gcc gcg cac ttg ggc ttc ttc gag ttc tac gtc     438
```

```
Arg Tyr Ile Ala Thr Ala Ala His Leu Gly Phe Glu Phe Tyr Val
120             125                 130                 135 acc agg gaa ggt tac cag ccc act gta ccg ctt aaa tgg gca gac ttg      486
Thr Arg Glu Gly Tyr Gln Pro Thr Val Pro Leu Lys Trp Ala Asp Leu
                140                 145                 150 gag gag ttg ccg ttc atc aac gtc acc aac ccc ccg ctt gtc agc ggc      534
Glu Glu Leu Pro Phe Ile Asn Val Thr Asn Pro Pro Leu Val Ser Gly
            155                 160                 165 tcc tac caa atc acc ggc acc acg cct tcc tgc aag tcc ggc agc cac      582
Ser Tyr Gln Ile Thr Gly Thr Thr Pro Ser Cys Lys Ser Gly Ser His
        170                 175                 180 gtc atg tac gtc ata tgg cag cgc acc gac agc ccc gaa gcc ttc cac      630
Val Met Tyr Val Ile Trp Gln Arg Thr Asp Ser Pro Glu Ala Phe His
    185                 190                 195 tcc tgc tcc gac gtc tac ttc act gat gcc ctc tct ctc cac tct acc      678
Ser Cys Ser Asp Val Tyr Phe Thr Asp Ala Leu Ser Leu His Ser Thr
200                 205                 210                 215 acc taggaggagg cgctctgtt gggccacttc tctctctctc tctctctctc            731
Thr tctctcgggg cagtgctctc gtgctcggaa tgctcctgta attacaataa gaaatgaaca    791
tgtttctttc gcctctctaa aaaaaaaaaa aaaaaaa                             828

<210> SEQ ID NO 2
<211> LENGTH: 651
<212> TYPE: DNA
<213> ORGANISM: Tectaria sp.
<220> FEATURE:
<221> NAME/KEY: CDS
<222> LOCATION: (1)..(648)

<400> SEQUENCE: 2 atg ggg agg tca tgg gga gtt gtg gct gtt atg gtg ttg tgc gcc agt      48
Met Gly Arg Ser Trp Gly Val Val Ala Val Met Val Leu Cys Ala Ser
1               5                   10                  15 ggc ctg ctg ggc ata gtg cgc ggc cat ggc agc atg gag gac ccc atc      96
Gly Leu Leu Gly Ile Val Arg Gly His Gly Ser Met Glu Asp Pro Ile
            20                  25                  30 agt cgc gtc tac aga tgc cgt cta gag aat ccg gag cgt ccc acg tcg      144
Ser Arg Val Tyr Arg Cys Arg Leu Glu Asn Pro Glu Arg Pro Thr Ser
        35                  40                  45 cca gct tgc caa gcg gcg gtg gcg ctc agt ggc act caa gcc ttc tat      192
Pro Ala Cys Gln Ala Ala Val Ala Leu Ser Gly Thr Gln Ala Phe Tyr
    50                  55                  60 gat tgg aat gag gcg aac att cct aac gcc gct ggc cgg cac cgc gag      240
Asp Trp Asn Glu Ala Asn Ile Pro Asn Ala Ala Gly Arg His Arg Glu
65                  70                  75                  80 ctc att ccg gat ggc caa ctg tgc agc gcc ggg cgg ttc aag ttt cgg      288
Leu Ile Pro Asp Gly Gln Leu Cys Ser Ala Gly Arg Phe Lys Phe Arg
                85                  90                  95 ggc ctc gac ttg gca cgc tcc gac tgg ata gcc acc ccc tcg ccc tcc      336
Gly Leu Asp Leu Ala Arg Ser Asp Trp Ile Ala Thr Pro Ser Pro Ser
            100                 105                 110 ggc gcc agc agc ttc cca ttc cgc tac ata gcc acc gcc gcg cac ttg      384
Gly Ala Ser Ser Phe Pro Phe Arg Tyr Ile Ala Thr Ala Ala His Leu
        115                 120                 125 ggc ttc ttc gag ttc tac gtc acc agg gaa ggt tac cag ccc act gta      432
Gly Phe Phe Glu Phe Tyr Val Thr Arg Glu Gly Tyr Gln Pro Thr Val
    130                 135                 140 ccg ctt aaa tgg gca gac ttg gag gag ttg ccg ttc atc aac gtc acc      480
Pro Leu Lys Trp Ala Asp Leu Glu Glu Leu Pro Phe Ile Asn Val Thr
145                 150                 155                 160
```

```
aac ccc ccg ctt gtc agc ggc tcc tac caa atc acc ggc acc acg cct    528
Asn Pro Pro Leu Val Ser Gly Ser Tyr Gln Ile Thr Gly Thr Thr Pro
            165                 170                 175 tcc tgc aag tcc ggc agc cac gtc atg tac gtc ata tgg cag cgc acc    576
Ser Cys Lys Ser Gly Ser His Val Met Tyr Val Ile Trp Gln Arg Thr
        180                 185                 190 gac agc ccc gaa gcc ttc cac tcc tgc tcc gac gtc tac ttc act gat    624
Asp Ser Pro Glu Ala Phe His Ser Cys Ser Asp Val Tyr Phe Thr Asp
    195                 200                 205 gcc ctc tct ctc cac tct acc acc tag                                651
Ala Leu Ser Leu His Ser Thr Thr
210                 215

<210> SEQ ID NO 3
<211> LENGTH: 579
<212> TYPE: DNA
<213> ORGANISM: Tectaria sp.
<220> FEATURE:
<221> NAME/KEY: CDS
<222> LOCATION: (1)..(576)

<400> SEQUENCE: 3 cat ggc agc atg gag gac ccc atc agt cgc gtc tac aga tgc cgt cta     48
His Gly Ser Met Glu Asp Pro Ile Ser Arg Val Tyr Arg Cys Arg Leu
1               5                   10                  15 gag aat ccg gag cgt ccc acg tcg cca gct tgc caa gcg gcg gtg gcg     96
Glu Asn Pro Glu Arg Pro Thr Ser Pro Ala Cys Gln Ala Ala Val Ala
            20                  25                  30 ctc agt ggc act caa gcc ttc tat gat tgg aat gag gcg aac att cct    144
Leu Ser Gly Thr Gln Ala Phe Tyr Asp Trp Asn Glu Ala Asn Ile Pro
        35                  40                  45 aac gcc gct ggc cgg cac cgc gag ctc att ccg gat ggc caa ctg tgc    192
Asn Ala Ala Gly Arg His Arg Glu Leu Ile Pro Asp Gly Gln Leu Cys
    50                  55                  60 agc gcc ggg cgg ttc aag ttt cgg ggc ctc gac ttg gca cgc tcc gac    240
Ser Ala Gly Arg Phe Lys Phe Arg Gly Leu Asp Leu Ala Arg Ser Asp
65                  70                  75                  80 tgg ata gcc acc ccc tcg ccc tcc ggc gcc agc agc ttc cca ttc cgc    288
Trp Ile Ala Thr Pro Ser Pro Ser Gly Ala Ser Ser Phe Pro Phe Arg
                85                  90                  95 tac ata gcc acc gcc gcg cac ttg ggc ttc ttc gag ttc tac gtc acc    336
Tyr Ile Ala Thr Ala Ala His Leu Gly Phe Phe Glu Phe Tyr Val Thr
            100                 105                 110 agg gaa ggt tac cag ccc act gta ccg ctt aaa tgg gca gac ttg gag    384
Arg Glu Gly Tyr Gln Pro Thr Val Pro Leu Lys Trp Ala Asp Leu Glu
        115                 120                 125 gag ttg ccg ttc atc aac gtc acc aac ccc ccg ctt gtc agc ggc tcc    432
Glu Leu Pro Phe Ile Asn Val Thr Asn Pro Pro Leu Val Ser Gly Ser
    130                 135                 140 tac caa atc acc ggc acc acg cct tcc tgc aag tcc ggc agc cac gtc    480
Tyr Gln Ile Thr Gly Thr Thr Pro Ser Cys Lys Ser Gly Ser His Val
145                 150                 155                 160 atg tac gtc ata tgg cag cgc acc gac agc ccc gaa gcc ttc cac tcc    528
Met Tyr Val Ile Trp Gln Arg Thr Asp Ser Pro Glu Ala Phe His Ser
                165                 170                 175 tgc tcc gac gtc tac ttc act gat gcc ctc tct ctc cac tct acc acc    576
Cys Ser Asp Val Tyr Phe Thr Asp Ala Leu Ser Leu His Ser Thr Thr
            180                 185                 190 tag                                                                579
```

<210> SEQ ID NO 4
<211> LENGTH: 216
<212> TYPE: PRT
<213> ORGANISM: Tectaria sp.

<400> SEQUENCE: 4

Met Gly Arg Ser Trp Gly Val Val Ala Val Met Val Leu Cys Ala Ser
1               5                   10                  15

Gly Leu Leu Gly Ile Val Arg Gly His Gly Ser Met Glu Asp Pro Ile
            20                  25                  30

Ser Arg Val Tyr Arg Cys Arg Leu Glu Asn Pro Glu Arg Pro Thr Ser
        35                  40                  45

Pro Ala Cys Gln Ala Ala Val Ala Leu Ser Gly Thr Gln Ala Phe Tyr
    50                  55                  60

Asp Trp Asn Glu Ala Asn Ile Pro Asn Ala Ala Gly Arg His Arg Glu
65                  70                  75                  80

Leu Ile Pro Asp Gly Gln Leu Cys Ser Ala Gly Arg Phe Lys Phe Arg
                85                  90                  95

Gly Leu Asp Leu Ala Arg Ser Asp Trp Ile Ala Thr Pro Ser Pro Ser
            100                 105                 110

Gly Ala Ser Ser Phe Pro Phe Arg Tyr Ile Ala Thr Ala Ala His Leu
        115                 120                 125

Gly Phe Phe Glu Phe Tyr Val Thr Arg Glu Gly Tyr Gln Pro Thr Val
    130                 135                 140

Pro Leu Lys Trp Ala Asp Leu Glu Glu Leu Pro Phe Ile Asn Val Thr
145                 150                 155                 160

Asn Pro Pro Leu Val Ser Gly Ser Tyr Gln Ile Thr Gly Thr Thr Pro
                165                 170                 175

Ser Cys Lys Ser Gly Ser His Val Met Tyr Val Ile Trp Gln Arg Thr
            180                 185                 190

Asp Ser Pro Glu Ala Phe His Ser Cys Ser Asp Val Tyr Phe Thr Asp
        195                 200                 205

Ala Leu Ser Leu His Ser Thr Thr
    210                 215

<210> SEQ ID NO 5
<211> LENGTH: 192
<212> TYPE: PRT
<213> ORGANISM: Tectaria sp.

<400> SEQUENCE: 5

His Gly Ser Met Glu Asp Pro Ile Ser Arg Val Tyr Arg Cys Arg Leu
1               5                   10                  15

Glu Asn Pro Glu Arg Pro Thr Ser Pro Ala Cys Gln Ala Ala Val Ala
            20                  25                  30

Leu Ser Gly Thr Gln Ala Phe Tyr Asp Trp Asn Glu Ala Asn Ile Pro
        35                  40                  45

Asn Ala Ala Gly Arg His Arg Glu Leu Ile Pro Asp Gly Gln Leu Cys
    50                  55                  60

Ser Ala Gly Arg Phe Lys Phe Arg Gly Leu Asp Leu Ala Arg Ser Asp
65                  70                  75                  80

Trp Ile Ala Thr Pro Ser Pro Ser Gly Ala Ser Ser Phe Pro Phe Arg
                85                  90                  95

Tyr Ile Ala Thr Ala Ala His Leu Gly Phe Phe Glu Phe Tyr Val Thr
            100                 105                 110

-continued

```
Arg Glu Gly Tyr Gln Pro Thr Val Pro Leu Lys Trp Ala Asp Leu Glu
        115                 120                 125

Glu Leu Pro Phe Ile Asn Val Thr Asn Pro Pro Leu Val Ser Gly Ser
    130                 135                 140

Tyr Gln Ile Thr Gly Thr Thr Pro Ser Cys Lys Ser Gly Ser His Val
145                 150                 155                 160

Met Tyr Val Ile Trp Gln Arg Thr Asp Ser Pro Glu Ala Phe His Ser
                165                 170                 175

Cys Ser Asp Val Tyr Phe Thr Asp Ala Leu Ser Leu His Ser Thr Thr
            180                 185                 190
```